United States Patent
Sherman et al.

(10) Patent No.: US 10,040,734 B2
(45) Date of Patent: Aug. 7, 2018

(54) PRODUCTION OF ISOBUTYLENE, ISOAMYLENE, OR ALKYLATES FROM MIXED ALKANES

(71) Applicant: REACTION 35, LLC, Santa Barbara, CA (US)

(72) Inventors: Jeffrey H. Sherman, Vero Beach, FL (US); Peter K. Stoimenov, Goleta, CA (US)

(73) Assignee: REACTION 35, LLC, Houston, TX (US)

( * ) Notice: Subject to any disclaimer, the term of this patent is extended or adjusted under 35 U.S.C. 154(b) by 0 days.

(21) Appl. No.: 15/511,969

(22) PCT Filed: Sep. 15, 2015

(86) PCT No.: PCT/US2015/050159
§ 371 (c)(1),
(2) Date: Mar. 16, 2017

(87) PCT Pub. No.: WO2016/044256
PCT Pub. Date: Mar. 24, 2016

(65) Prior Publication Data
US 2017/0291864 A1    Oct. 12, 2017

Related U.S. Application Data

(60) Provisional application No. 62/051,005, filed on Sep. 16, 2014.

(51) Int. Cl.
| | | |
|---|---|---|
| *C07C 17/23* | (2006.01) | |
| *C07C 17/10* | (2006.01) | |
| *C07C 11/02* | (2006.01) | |
| *C07C 1/30* | (2006.01) | |
| *C07C 5/44* | (2006.01) | |

(52) U.S. Cl.
CPC ............... *C07C 17/23* (2013.01); *C07C 1/30* (2013.01); *C07C 5/44* (2013.01); *C07C 11/02* (2013.01); *C07C 17/10* (2013.01); *C07C 2527/08* (2013.01)

(58) Field of Classification Search
CPC ......... C07C 11/02; C07C 17/10; C07C 17/23; C07C 1/30; C07C 2527/08; C07C 5/2789; C07C 5/44; C07C 11/09; C07C 11/10; C07C 19/075; C07C 2527/125; C07C 9/12; C07C 9/18
See application file for complete search history.

(56) References Cited

U.S. PATENT DOCUMENTS

| | | | |
|---|---|---|---|
| 3,246,043 | A | 4/1966 | De Rosset |
| 5,406,018 | A | 4/1995 | Sherman |
| 2003/0125585 | A1 | 7/2003 | Yilmaz et al. |
| 2005/0171393 | A1 | 8/2005 | Lorkovic |
| 2010/0099930 | A1 | 4/2010 | Stoimenov et al. |
| 2012/0302808 | A1 | 11/2012 | Julka et al. |

FOREIGN PATENT DOCUMENTS

GB      591632 A      8/1947

OTHER PUBLICATIONS

International Search Report and Written Opinion issued in PCT/US2015/050159, dated Jan. 22, 2016 (13 pages).
Extended European Search Report issued in Application No. 15841725.3, dated Feb. 27, 2018, 6 pages.

*Primary Examiner* — Sharon Pregler
(74) *Attorney, Agent, or Firm* — Adolph Locklar

(57) ABSTRACT

A method includes brominating a butanes feed stream including i-butane in a bromination reactor to form a bromination effluent stream including t-butyl bromide. The method includes dehydrobrominating the t-butyl bromide to form isobutylene. Another method includes brominating a mixed pentanes feed stream including i-pentane and n-pentane in a bromination reactor to form a bromination effluent stream including t-pentyl bromide. The method includes dehydrobrominating the t-pentyl bromide to form isoamylene and HBr.

21 Claims, 3 Drawing Sheets

PRODUCTION OF ISOBUTYLENE, ISOAMYLENE, OR ALKYLATES FROM MIXED ALKANES

CROSS-REFERENCE TO RELATED APPLICATIONS

This application is a National Stage Entry of PCT/US2015/050159, filed Sep. 15, 2015; which itself claims priority from U.S. provisional application No. 62/051,005, filed Sep. 16, 2014. The entireties of both PCT/US2015/050159 and U.S. 62/051,005 are incorporated herein by reference.

FIELD

The present disclosure generally relates to the formation of alkanes and alkenes from mixed alkanes. More particularly, the present disclosure relates to the formation of isobutylene, isoamylene, or alkylates from mixed alkanes.

BACKGROUND

One conventional method of obtaining isobutylene is from a crude $C_4$ stream ($CC_4$) produced as a co-product of ethylene in a steam cracking process. The crude $C_4$ stream is a mixture of $C_4$ olefins, di-olefins and saturated hydrocarbons, with the quantity of $CC_4$ and the relative proportions of the $CC_4$ components dependent on the cracker feedstock and operating conditions. Typically, a series of extraction steps are performed to separate the isobutylene from the $CC_4$.

Isobutylene may also be obtained through the dehydrogenation of isobutane ("the iBDH process"). In the process, isobutane may be decomposed over a catalyst to produce isobutylene and hydrogen. Separation and recovery of isobutylene from the reactor effluent of the iBDH process is performed by reacting the effluent with an alcohol to form an ether, which is then separated from the remainder of the reactor effluent. Isobutylene is recovered following the cracking of the ether, which also regenerates the alcohol.

Isobutane may also be used to produce alkanes of a sufficient octane number and vapor pressure for gasoline-type fuels through alkylation, in alkylation, isobutane may be reacted with olefins, such as butenes or propylene, to form branched alkanes. Traditionally, the olefins used in alkylation have been obtained from other processes used in the petrochemical or petroleum refining industries. For example, propylene and butenes may be produced in steam crackers utilizing naphtha as a feedstock, while propylene may also be obtained as a byproduct of fluid catalytic cracking.

BRIEF DESCRIPTION OF THE DRAWINGS

The present disclosure is best understood from the detailed description when read with the accompanying figures. In accordance with the standard practice in the industry, various features are not drawn to scale.

SUMMARY

Figure 1:
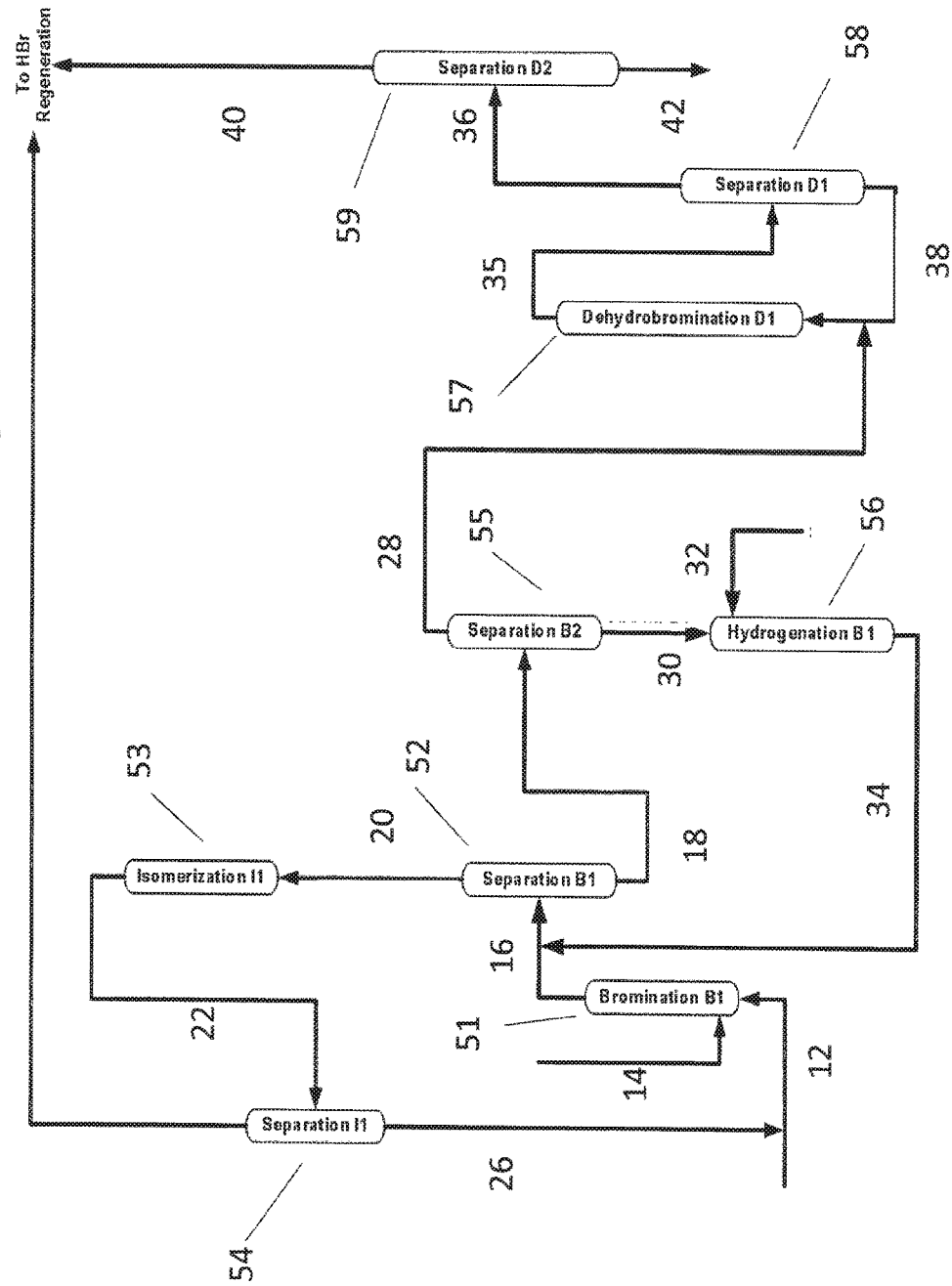
FIG. 1 is a process flow diagram depicting an isobutylene production system consistent with at least one embodiment of the present disclosure.

In an embodiment, a method is disclosed. The method includes brominating a butanes feed stream including i-butane in a bromination reactor to form a bromination effluent stream including t-butyl bromide. The method includes dehydrobrominating the t-butyl bromide to form isobutylene and HBr.

In another embodiment, a method is disclosed that includes brominating a mixed pentanes feed stream including i-pentane and n-pentane in a bromination reactor to form a bromination effluent stream including t-pentyl bromide. The method includes dehydrobrominating the t-pentyl bromide to form isoamylene and HBr.

In another embodiment, a method is disclosed. The method includes brominating a butanes feed stream including i-butane in a bromination reactor to form a bromination effluent stream including t-butyl bromide. The method further includes reacting the t-butyl bromide in a coupling reactor to form isooctane, isooctene, and brominated species of isooctane and isooctene.

DETAILED DESCRIPTION

The following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

A "bromide" is a hydrocarbon having at least one bromine atom substitution.

A "monobromide" is a hydrocarbon having only one bromine atom substitution.

A "polybromide" is a hydrocarbon having more than one bromine atom substitution.

"Butanes" are a mixture of isobutane (i-butane) and normal butane (n-butane).

"Pentanes" are a mixture of isopentane (i-pentane) and normal pentane (n-pentane).

"Alkylates" are molecules resulting from the addition of an alkyl group to a molecule.

"Isoamylene" is also described as 2-methyl-2-butene.

"i-pentyl bromide" is also described as 2-bromo-2-methylbutane or i-amyl bromide.

In certain embodiments of the present disclosure, isobutylene is produced from isobutane (i-butane) or a mixed stream containing i-butane and normal butane n-butane). FIG. 1 is a process flow diagram depicting isobutylene production system 10 consistent with certain embodiments of the present disclosure. Butanes feed stream 12 includes i-butane. Butanes feed stream 12 may include a mixture of i-butane and n-butane, in which a molar ratio of i-butane to n-butane ranges from 1:0.01 to 0.01:1, or from 1:0.1 to 0.1:1, or from 1:0.5 to 0.5:1, or from 1:0 to 0:1, for example. Butanes feed stream 12 is fed to Bromination B1 51, a bromination reactor. The i-butane or mixture of i-butane and n-butane is reacted with bromine from bromine source stream 14 in Bromination B1 51 to form bromides. Bromine source stream 14 and butanes feed stream 12 may be added separately to Bromination B1 51 or mixed prior to entry into Bromination B1.

Conditions for the bromination reaction in Bromination B1 51 may be selected to: i) maximize the yield of i-butyl bromide (2-bromo-2-methylpropane) and 1-bromo-2-methylpropane; ii) minimize the formation of n-butyl bromides; and iii) minimize the formation of i-butane and n-butane polybromides. Polybromides include dibromides, tribromides, and/or tetrabromides of i-butane and n-butane. Because the bromination reaction is exothermic, Bromination B1 51 may be cooled to maintain the bromination reaction within a desired temperature range. In certain embodiments, the bromination reaction is carried out in a shell and tube reactor in which bromine source stream 14 and butanes feed stream 12 are introduced into Bromination B1 Si at a temperature greater than or equal to 200° C., greater than or equal to 130° C., or from 130° C. to 200° C. In some embodiments, the bromination reaction is carried out in liquid phase at a temperature of 130° C. or greater. A bromination reaction may be carried out inside the tubes, and steam may then be generated on the shell side of the shell and tube reactor in order to limit the maximum temperature of Bromination B1 51 to the desired temperature range, such as 250° C.-350° C. The generated steam may be used elsewhere in the process.

In certain embodiments of the present disclosure, a stoichiometric excess of the butane may be used to decrease selectivity to polybromides and/or to limit temperature rise in the bromination reaction. In other embodiments of the present disclosure, the bromination reaction is carried out in one or more adiabatic reactors with cooling between the different adiabatic reactors. This cooling may be achieved using heat exchanger(s) or cold (~35° C.) bromine or butanes. In certain other embodiments of this disclosure, cold (~35° C.) bromine is introduced at multiple positions along a length of Bromination B1 51 to keep the bromination reaction temperature within the desired range. In certain embodiments, this reaction is carried out at higher than atmospheric pressure. In certain other embodiments, this pressure is near that required for subsequent downstream separations. Having the pressure near that required for subsequent downstream separations may significantly improve the efficiency of the entire process by reducing or eliminating any required downstream compression prior to separation. Use of certain pressures may reduce the cooling used to condense the overhead stream in separation. In certain embodiments, cooling water may be used for condensing the overhead stream, rather than refrigeration, in other embodiments, refrigeration may be used for condensing the overhead stream. In certain embodiments, a combination of cooling water and refrigeration may be used for condensing the overhead stream. For example and without limitation, in some embodiments a pressure of at least 30 bar, or from 30 bar to 40 bar, or from 30 bar to 35 bar, or about 30 bar may be used for condensing the overhead stream. In embodiments in which the pressure is at least 30 bar, cooling water may be used for condensing the overhead stream. In embodiments in which the pressure is at least 30 bar, condensing the overhead stream in separation may be performed without use of refrigerant, such as propane. In some embodiments a pressure of from greater than 10 bar to less than 30 bar, or from 15 bar to 25 bar, or about 20 bar may be used for condensing the overhead stream. In embodiments in which the pressure is greater than 10 bar and less than 30 bar, a combination of cooling water and refrigerant, such as propane, may be used for condensing the overhead stream. In embodiments in which the pressure is greater than 10 bar and less than 30 bar, the overhead stream may be cooled to a temperature of from greater than 0° C. to less than 30° C., or from 15° C. to 25° C., or about 20° C. for condensing the overhead stream. In some embodiments a pressure of from greater than 0 bar to at most 10 bar, or from 5 bar to 10 bar, or from 7 bar to 10 bar may be used for condensing the overhead stream in separation, in embodiments in which the pressure is greater than 0 bar and at most 10 bar, a refrigerant, such as propane, may be used for condensing the overhead stream without use of cooling water. In embodiments in which the pressure is greater than 0 bar and at most 10 bar, the overhead stream may be cooled to a temperature of less than 0° C. Bromination B1 51 may be divided into a cooled section and an adiabatic section.

Bromides and HBr formed in Bromination B1 51 and unreacted butanes are discharged from Bromination B1 51 through Bromination B1 effluent 16. Bromination B1 effluent 16 enters Separation B1 52 where the reaction products of Bromination B1 51 are separated. For example and without limitation, Bromination B1 effluent 16 may be separated by distillation into two streams including: brominated compounds 18, which include the bromides formed in the bromination reaction, and isomerization feed stream 20, which includes HBr, and unreacted n-butane and i-butane. In certain embodiments, isomerization feed stream 20 has a lower ratio of i-butane to n-butane than butanes feed stream 12.

Isomerization feed stream 20 may be isomerized over an isomerization catalyst, such as, for example, $AlBr_3$ in Isomerization I1 53, an isomerization reactor. In some embodiments, isomerization of isomerization feed stream 20 occurs in liquid phase with an isomerization catalyst (e.g., $AlBr_3$), which may be dissolved. Isomerization of isomerization feed stream 20 converts at least a portion of the n-butane to i-butane and increases the ratio of i-butane to n-butane over that in isomerization feed stream 20. The HBr in Isomerization I1 effluent 22 may be recovered in Separation I1 54 and transferred, for instance to HBr regeneration equipment through Separation I1 HBr stream 24. The n-butane and i-butane in Isomerization I1 effluent 22 may be recycled to Bromination B1 51 through butane recycle stream 26 from Separation I1 54. In some embodiments, the amount of HBr present in isomerization feed stream 20 is reduced prior to being fed to Isomerization I1 53. For example and without limitation, isomerization feed stream 20 may be subjected separation, such as by distillation, to remove at least a portion of HBr prior to entering Isomerization I1 53. In some embodiments, all or substantially all of HBr is removed from isomerization feed stream 20 prior to entering Isomerization I1 53. In some embodiments, HBr is not separated from isomerization feed stream 20 prior to entering Isomerization I1 53.

Following separation in Separation B1 52, brominated compounds 18 may be directed to Separation B2 55, where the brominated compounds 18 are separated, such as by distillation, into two streams including: monobrominated stream 28, which may contain t-butyl bromide and n-butyl bromide, and recycle bromides stream 30, which may include isobutane polybromides.

Recycle bromides stream 30 may be partially hydrogenated with hydrogen from hydrogen stream 32 to t-butyl bromide and n-bromobutane in Hydrogenation B1 56. Recycle bromides stream 30 may be completely hydrogenated with hydrogen from hydrogen stream 32 to i-butane and n-butane in the presence of a catalyst in Hydrogenation B1 56. For example and without limitation, the hydrogenation catalyst may be Pd, Pt, Ni, Ru, Rh, Cu, or another hydrogenation catalyst known to one skilled in the art. The hydrogenation reaction may be carried out in the presence of HBr to improve the selectivity to t-butyl bromide and bromobutane and minimize coke formation. Hydrogenation products stream 34 may be recycled to Separation B1 52. In certain embodiments (not shown) HBr may be recovered from hydrogenation products stream 34 and the remainder of hydrogenation products stream 34 may be recycled to Separation B1 52.

Monobrominated stream 28 may be fed to Dehydrobromination D1 57, a dehydrobromination reactor. In Dehydrobromination D1 57, t-butyl bromide may be converted to isobutylene. In certain embodiments of the present disclosure, the dehydrobromination reaction is performed thermally in the absence of a catalyst, i.e., non-catalytically. However, in certain circumstances, a thermal reaction in Dehydrobromination D1 57 may be slow. Such slow reaction rates may require long residence times and/or high temperature in order to achieve suitable conversion. In some embodiments, the reaction in Dehydrobromination D1 57 may be carried out in the presence of a catalyst, such as a silica-based catalyst. One example of a suitable silica-based catalyst is WR Grace Silica 1151, available from W. R. Grace &. Co. In order to shift the equilibrium in the desired direction, in certain embodiments, the reaction is carried out at a temperature of 250° C.-500° C. In certain embodiments, the dehydrobromination reaction is carried out at higher than atmospheric pressure. In certain other embodiments, the pressure is near that required for subsequent downstream separations. Having the pressure near that required for subsequent downstream separations significantly improves the efficiency of the entire process by reducing or eliminating any required downstream compression prior to separation. Use of certain pressures may reduce the cooling used to condense the overhead stream in separation. In certain embodiments, cooling water may be used for condensing the overhead stream, rather than refrigeration. In other embodiments, refrigeration may be used for condensing the overhead stream. In certain embodiments, a combination of cooling water and refrigeration may be used for condensing the overhead stream. For example and without limitation, in some embodiments a pressure of at least 30 bar, or from 30 bar to 40 bar, or from 30 bar to 35 bar, or about 30 bar may be used for condensing the overhead stream. In embodiments in which the pressure is at least 30 bar, cooling water may be used for condensing the overhead stream. In embodiments in which the pressure is at least 30 bar, condensing the overhead stream in separation may be performed without use of refrigerant, such as propane. In some embodiments a pressure of from greater than 10 bar to less than 30 bar, or from 15 bar to 25 bar, or about 20 bar may be used for condensing the overhead stream. In embodiments in which the pressure is greater than 10 bar and less than 30 bar, a combination of cooling water and refrigerant, such as propane, may be used for condensing the overhead stream. In embodiments in which the pressure is greater than 10 bar and less than 30 bar, the overhead stream may be cooled to a temperature of from greater than 0° C. to less than 30° C., or from 15° C. to 25° C., or about 20° C. for condensing the overhead stream. In some embodiments a pressure of from greater than 0 bar to at most 10 bar, or from 5 bar to 10 bar, or from 7 bar to 10 bar may be used for condensing the overhead stream in separation. In embodiments in which the pressure is greater than 0 bar and at most 10 bar, a refrigerant, such as propane, may be used for condensing the overhead stream without use of cooling water. In embodiments in which the pressure is greater than 0 bar and at most 10 bar, the overhead stream may be cooled to a temperature of less than 0° C.

The effluent of Dehydrobromination D1 57, dehydrobromination effluent 35, includes isobutylene, HBr, and unconverted t-butyl bromide. The dehydrobromination effluent 35 may be directed to Separation D1 58, where dehydrobromination effluent 35 is separated, such as by distillation, into crude product stream 36, which includes isobutylene and HBr, and dehydrobromination recycle 38, which includes t-butyl bromide that was not converted in Dehydrobromination D1 57. Dehydrobromination effluent 35 may be rapidly cooled, for example, by contacting with cold (~35° C.) t-butyl bromide. Without being bound by theory, it is believed that rapid cooling reduces the formation of t-butyl bromide through the reaction of HBr and isobutylene. Dehydrobromination recycle 38 may be recycled to Dehydrobromination D1 57.

Crude product stream 36 may be directed to Separation D2 59, where the isobutylene product is separated, such as by distillation, from HBr and recovered. HBr leaves Separation D2 59 as HBr stream 40. The isobutylene may be discharged from Separation D2 59 through isobutylene product stream 42.

In certain embodiments of the present disclosure, HBr generated in isobutylene production system 10, such as Separation I1 HBr stream 24 and HBr stream 40, may be regenerated, for example, by oxidation, to form bromine, which may be combined with bromine source stream 14.

Figure 2:
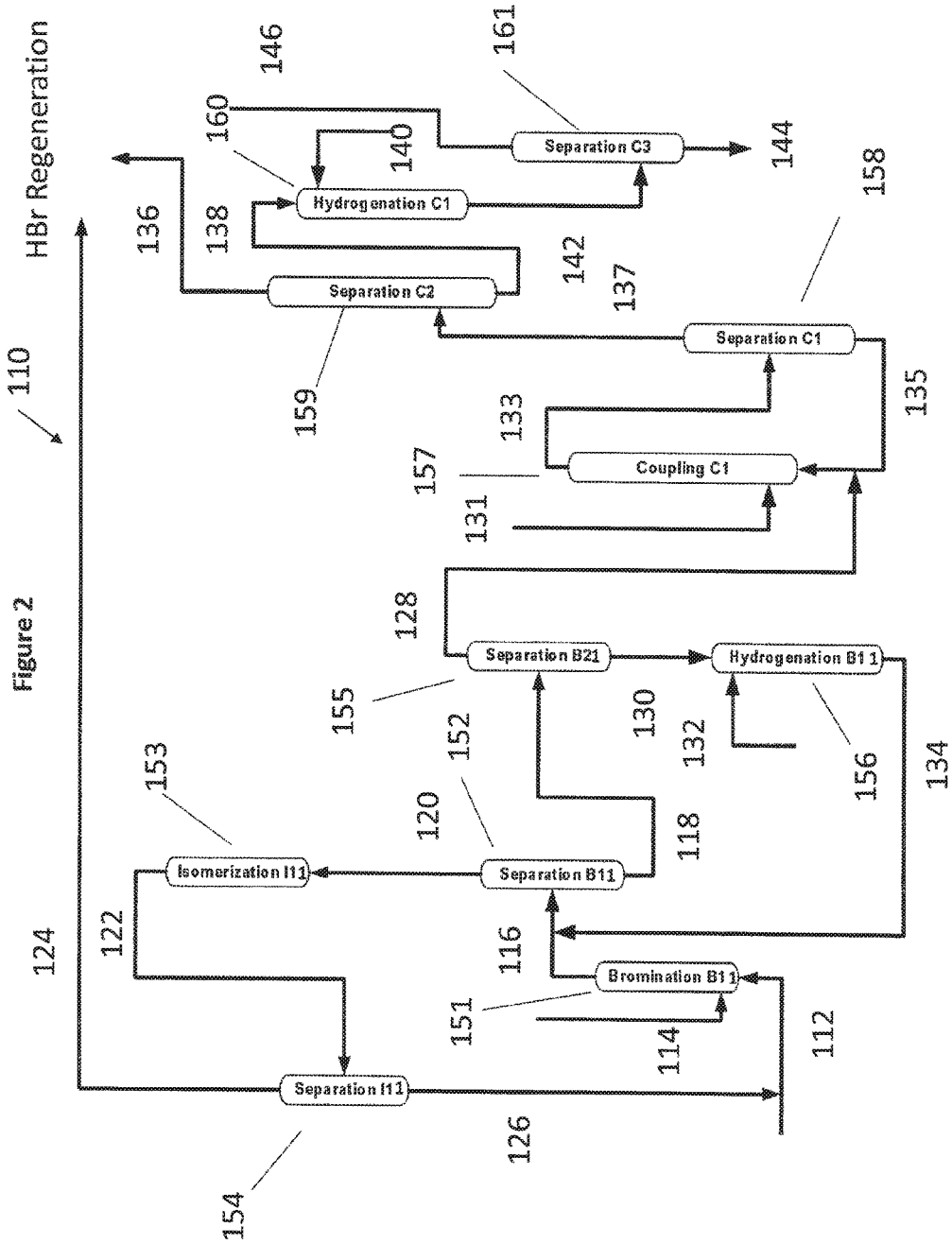
FIG. 2 is a process flow diagram depicting an alkylate production system consistent with at least one embodiment of the present disclosure.

In another embodiment of the present disclosure, isooctane and other high-octane alkanes and alkenes may be formed from a mixed butane feedstock. FIG. 2 is a process flow diagram depicting alkylate production system 110 consistent with certain embodiments of the present disclosure. Butanes feed stream 112 includes i-butane. Butanes feed stream 112 may include a mixture of i-butane and n-butane in which the molar ratio of i-butane to n-butane ranges from 1:0.01 to 0.01:1, or 1:0.1 to 0.1:1, or 1:0.5 to 0.5:1, or 1:0 to 0:1, for example. The butanes feed stream 112 may be fed to Bromination B11 151, a bromination reactor. The i-butane or the mixture of i-butane and n-butane is reacted with bromine from bromine source stream 114 in Bromination B11 151 to form bromides. Bromine source stream 114 and butanes feed stream 112 may be added separately to Bromination B11 151 or mixed prior to entry into bromination B11 151.

In certain embodiments, conditions for the bromination reaction in Bromination B11 151 are selected to: i) maximize the yield of t-butyl bromide (2-bromo-2-methylpropane) and 1-bromo-2-methylpropane; ii) minimize the formation of n-butyl bromides; and iii) minimize the formation of polybromides of isobutane. The polybromides may include dibromides, tribromides, and/or tetrabromides of i-butane and n-butane. In other embodiments, conditions for the bromination reaction are selected to: i) maximize the yield of t-butyl bromide (2-bromo-2-methylpropane), 1-bromo-2-methylpropane, and n-butyl bromides; and ii) minimize the formation of polybromides of isobutane, such as di, tri, and/or tetrabromides of isobutane. In other embodiments, conditions for the bromination reaction may be selected to: control the yield of t-butyl bromide (2-bromo-2-methylpropane) and 1-bromo-2-methylpropane, relative to the yield of n-butyl bromides; and ii) minimize the formation of polybromides of isobutane; such as isobutane di, tri, and/or tetrabromides. For example and without limitation, the temperature of the bromination reaction may be controlled. Without being bound by theory, lower reaction temperatures may tend to result in a higher production of t-butyl bromide than n-butyl bromide. Because the bromination reaction is exothermic, Bromination B11 151 may be cooled to maintain the bromination reaction within the desired temperature range. In certain embodiments, the bromination reaction is carried out in a shell and tube reactor in which bromine source stream 114 and butanes feed stream 112 are introduced into Bromination. B11 151 at a temperature greater than or equal to 200° C. The bromination reaction may be carried out inside the tubes of the shell and tube reactor, and steam may then be generated on the shell side of the shell and tube reactor in order to limit the maximum temperature of Bromination B11 151 to the desired temperature range, such as 250° C.-350° C. The generated steam of Bromination B11 151 may be used elsewhere in the process.

In certain embodiments of the present disclosure, a stoichiometric excess of the butanes may be used to decrease selectivity to polybromides and/or to limit temperature rise in Bromination B11 151. In other embodiments of the present disclosure, the bromination reaction is carried out in one or more adiabatic reactors with cooling between the different adiabatic reactors. This cooling may be achieved using heat exchanger(s) or cold (~35° C.) bromine or butanes. In certain other embodiments of this disclosure, cold (~35° C.) bromine is introduced at multiple positions along a length of Bromination B11 151 to keep the bromination reaction temperature within the desired range. In certain embodiments, the bromination reaction is carried out at higher than atmospheric pressure. In certain other embodiments, this pressure is near that required for subsequent downstream separations. Having the pressure near that required for subsequent downstream separations may significantly improve the efficiency of the entire process by reducing or eliminating any required downstream compression prior to separation. Use of certain pressures may reduce the cooling used to condense the overhead stream in separation. In certain embodiments, cooling water may be used for condensing the overhead stream, rather than refrigeration. In other embodiments, refrigeration may be used for condensing the overhead stream. In certain embodiments, a combination of cooling water and refrigeration may be used for condensing the overhead stream. For example and without limitation, in some embodiments a pressure of at least 30 bar, or from 30 bar to 40 bar, or from 30 bar to 35 bar, or about 30 bar may be used for condensing the overhead stream. In embodiments in which the pressure is at least 30 bar, cooling water may be used for condensing the overhead stream. In embodiments in which the pressure is at least 30 bar, condensing the overhead stream in separation may be performed without use of refrigerant, such as propane. In some embodiments a pressure of from greater than 10 bar to less than 30 bar, or from 15 bar to 25 bar, or about 20 bar may be used for condensing the overhead stream. In embodiments in which the pressure is greater than 10 bar and less than 30 bar, a combination of cooling water and refrigerant, such as propane, may be used for condensing the overhead stream. In embodiments in which the pressure is greater than 10 bar and less than 30 bar, the overhead stream may be cooled to a temperature of from greater than 0° C. to less than 30° C., or from 15° C. to 25° C., or about 20° C. for condensing the overhead stream. In some embodiments a pressure of from greater than 0 bar to at most 10 bar, or from 5 bar to 10 bar, or from 7 bar to 10 bar may be used for condensing the overhead stream in separation. In embodiments in which the pressure is greater than 0 bar and at most 10 bar, a refrigerant, such as propane, may be used for condensing the overhead stream without use of cooling water. In embodiments in which the pressure is greater than 0 bar and at most 10 bar, the overhead stream may be cooled to a temperature of less than 0° C. The bromination reactor. Bromination B11 151, may be divided into a cooled section and an adiabatic section.

Bromination B11 effluent 116 may include t-butyl bromide. In some embodiments, bromination B11 effluent 116 includes isobutyl bromide. Bromination B11 effluent 116 enters Separation B11 152 where the reaction products of Bromination B11 151 are separated, such as by distillation, into two streams including: brominated compounds 118, which include the bromides formed in the bromination reaction, and isomerization feed stream 120, which includes HBr, n-butane and i-butane. In certain embodiments, isomerization feed stream 120 has a lower ratio of i-butane to n-butane than that in the butanes feed stream 112.

Isomerization feed stream 120 is isomerized over an isomerization catalyst, such as, for example, $AlBr_3$ in Isomerization I11 153, an isomerization reactor. In some embodiments, isomerization of isomerization feed stream 120 occurs in liquid phase with an isomerization catalyst, for example, $AlBr_3$, which may be dissolved. Isomerization of isomerization feed stream 120 converts at least a portion of the n-butane to i-butane and increases the ratio of i-butane to n-butane over that in isomerization feed stream 120. The HBr in Isomerization I11 effluent 122 may be recovered in Separation I11 154 and transferred, for instance to HBr regeneration equipment through Separation I11 HBr stream 124. The butanes in Isomerization I11 effluent 122 may be recycled to Bromination B11 151 through butane recycle stream 126 from Separation I11 154. In some embodiments, the amount of HBr present in isomerization feed stream 120 is reduced prior to being fed to Isomerization I11 153. For example and without limitation, isomerization feed stream 120 may be subjected separation, such as by distillation, to remove at least a portion of HBr prior to entering Isomerization I11 153. In some embodiments, all or substantially all HBr is removed from isomerization teed stream 120 prior to entering Isomerization I11 153. In some embodiments, HBr is not separated from isomerization feed stream 120 prior to entering Isomerization I11 153.

Following separation in Separation B11 152, brominated compounds 118 may be directed to Separation B21 155, where the brominated compounds 118 are separated, such as by distillation, into two streams including: monobrominated stream 128, which may contain t-butyl bromide, and n-butylbromide, and recycle bromides stream 130, which may include polybromides.

Recycle bromides stream 130 may be partially hydrogenated with hydrogen from hydrogen stream 132 to t-butyl bromide and n-butyl bromide in Hydrogenation B11. Recycle bromides stream 130 may be completely hydrogenated with hydrogen from hydrogen stream 132 to i-butane and n-butane in the presence of a catalyst in Hydrogenation B11 156. For example and without limitation, the hydrogenation catalyst may be Pd, Pt, Ni, Ru, Rh, Cu, or another hydrogenation catalyst known to one skilled in the art. The hydrogenation reaction may be carried out in the presence of HBr to improve the selectivity to t-butyl bromide and bromobutane and minimize coke formation. Hydrogenation products stream 134 may be recycled to Separation B11 152. In certain embodiments (not shown) HBr may be recovered from hydrogenation products stream 134 and the remainder of hydrogenation products stream 134 may be recycled to Separation B11 152.

Monobrominated stream 128 may then be directed to Coupling C1 157 (a coupling reactor), wherein at least a portion of the t-butyl bromide, or t-butyl bromide and n-butyl bromide, are converted into a mixture of hydrocarbons including olefins, alkyl bromides and alkanes with multiples of eight carbon atoms, such as octane, isooctane, isooctene and HBr. During the coupling reaction, the t-butyl bromides and n-butyl bromides may be coupled to form olefins, alkyl bromides and alkanes having a greater number of carbon atoms than the alkyl bromides in Bromination B11 effluent 116. In certain embodiments, by varying the content of n-butyl bromide and t-butyl bromide produced in Bromination B11 151, the octane rating of the products of the coupling reaction in Coupling C1 157 may be controlled. Without being bound by theory, typically, the higher the concentration of t-butyl bromide molecules in monobrominated stream 128, all other conditions equal, the higher the octane rating of the mixture in coupling products stream 137.

In certain embodiments, a catalyst may be employed in Coupling C1 157. The catalyst employed in Coupling C1 157 may include or consist of non-crystalline alumino silicates (amorphous solid acids); tungsten/zirconia super acids; sulfated zirconia; zeolites, such as SAPO-34 and its framework-substituted analogues (optionally substituted with, e.g., Ni or Mn); ZSM-5 and its ion-exchanged analogs; an ion exchange resin; or framework substituted. ZSM-5 (optionally substituted with Ti, Fe, Ti+Fe, B, or Ga). A specific non-limiting example of a coupling catalyst is ion-exchanged ZSM-5 having a $SiO_2/Al_2O_3$ ratio below about 300, below about 100, or about 30 or less. Non-limiting examples of exchanged ions of the ion-exchanged ZSM-5 include ions of Ag, Ba, Bi, Ca, Fe, Li, Mg, Sr, Na, Rb, Mn, Co, Ni, Cu, Ru, Pb, Pd, Pt, and Ce. The exchanged ions may be exchanged as pure salts or as mixtures of salts. The preparation of doped zeolites and their use as carbon-carbon coupling catalysts is described in U.S. Patent Publication No. US 2005/0171393 A1, which is incorporated by reference herein in its entirety. In some embodiments, a fluorinated alumina based solid reactant, as described in more detail below, may be used as the coupling catalyst or as a support for a catalytic material useful in the formation of higher hydrocarbon products. Without being bound by theory, use of a fluorinated alumina may allow for the simultaneous formation of higher hydrocarbons and capture of hydrogen halide formed in the coupling reaction.

In some embodiments, an Mn-exchanged ZSM-5 zeolite having a $SiO_2/Al_2O_3$ ratio of 30 is used as the coupling catalyst. In other embodiments, a reduced aluminum content zeolite, such as a ZSM-5 zeolite, may be used as the coupling catalyst. Without being bound by theory, use of a dealuminated zeolite may result in hydrocarbons with a higher amount of paraffins than a zeolite of the same type that has not been dealuminated. Dealumination of a zeolite catalyst may be accomplished by selective treatment of a hydrogen-exchanged zeolite with a compound that specifically reacts with aluminum centers by forming either volatile compounds at high temperature or soluble complexes when treated in an aqueous solution. Examples of dealumination agents may include mineral acids, such as hydrochloric acid (HCl), hydrofluoric acid (HF), ethylenediaminetetraacetic acid (EDTA), oxalic acid, and malonic acid; overheated water steam (steaming); and exchange reagents (e.g., $SiCl_4$, $NH_4[SiF_6]$, $NH_4HF_2$, $AlF_3$, trialkyl phosphates, or organic phosphites).

A non-limiting example of a cation exchange resin coupling catalyst includes sulfonated polystyrene that has been cross-linked with divinylbenzene. Sulfonation of the polystyrene may result in formation of sulfonic acid groups on the resin. The properties of a polystyrene resin may be determine in part by the percentage of the cross-linking agent incorporated into the polystyrene resin. Additionally, the cation exchange capacity of the resin may be determined by the number of sulfonic acid groups that appear in the resin. Without being bound by theory, the use of a resin with a higher percentage of cross-linking agent may reduce swelling of the resin when in operation as a coupling catalyst. Additionally using a resin with a lower cation exchange capacity may suppress the formation of higher carbon number products.

In embodiments in which a catalyst is employed in Coupling C1 157, Coupling C1 157 may be a fixed bed, fluidized bed, or other suitable reactor. Coupling C1 157 may operate at: a temperature, such as from 120-300° C. or from 225-275° C.; a pressure, such as from 2-100 atmospheres or from 15-50 atmospheres; and a residence time, such as from about 1 second to about 45 seconds. Without being bound by theory, longer residence times may favor conversion of reactants to products, as well as product selectivity, while shorter residence times may result in higher throughput.

In certain embodiments, coupling reaction in Coupling C1 157 may be performed thermally in the absence of a catalyst, i.e., non-catalytically. When the coupling reaction is performed without a catalyst, Coupling C1 157 may operate at a temperature, such as from 120-500° C. or from 180-400° C.; a pressure, such as from 2-100 atmospheres or from 15-50 atmospheres; and a residence time, such as from about 1 second to about 180 seconds.

In certain embodiments, hydrogen ($H_2$) may be added to Coupling C1 157 through hydrogen coupling feed 131 to reduce coking. Hydrogen addition may also suppress the formation of higher carbon number products and reduce the olefinic content of the hydrocarbon mixture formed in Coupling C1 157. The nature of the hydrocarbon mixture formed in Coupling C1 157 may also be modified through the selection of the operating pressure and temperature of the reaction.

Coupling C1 effluent 133 may be directed to Separation C1 158 where Coupling C1 reaction products may be separated, such as by distillation, into coupling products stream 137, which may include isooctane, isooctene, and brominated species of each, their structural isomers and HBr; and coupling recycle 135, including t-butyl bromide and n-butyl bromide that was not reacted in Coupling C1 157. Coupling recycle 135 may be recycled to Coupling C1 157.

Coupling products stream 137 may be directed to Separation C2 159. Within Separation C2 159, HBr may be removed as Separation C2 HBr stream 136 and directed to HBr Regeneration. Mixed product stream 138; which may include isooctanes, isooctenes, and brominated species of each, may be directed to Hydrogenation C1 160. In Hydrogenation C1 160; olefins and alkyl bromides may be converted to the corresponding alkane by hydrogenation from hydrogen in Hydrogenation C1 hydrogen stream 140. Hydrogenation C1 discharge 142 may include alkylates, such as isooctanes, HBr, and isooctenes.

Hydrogenation C1 discharge 142 may be directed to Separation C3 161 where isooctanes and any remaining isooctenes are separated from HBr. Separation C3 HBr stream 146 may be directed to HBr Regeneration, whereas isooctanes and any remaining isooctenes may be discharged from Separation C3 through alkylation product stream 144.

In some embodiments; conditions for the bromination reaction are selected to i) maximize the yield of t-butyl bromide; ii) minimize the formation of polybromides of isobutane, such as di, tri, and/or tetrabromides of isobutane; and iii) minimize the formation of any n-butyl bromides. In such embodiments, alkylation product stream 144 may contain primarily dimerized isobutane.

Figure 3:
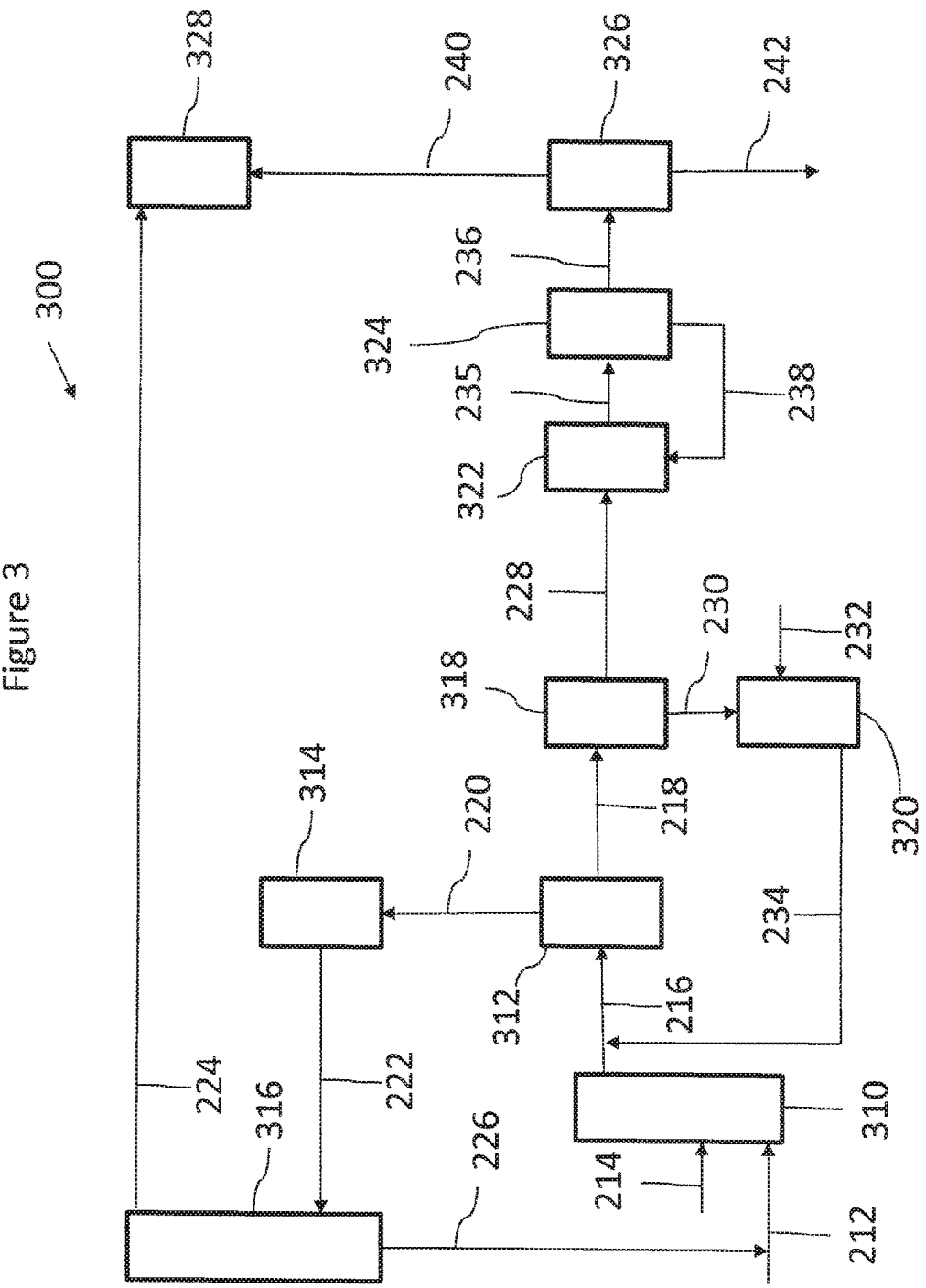
FIG. 3 is a process flow diagram depicting an isoamylene production system consistent with at least one embodiment of the present disclosure.

In certain embodiments of the present disclosure, isoamylene (2-methyl-2-butene) is produced from isopentane (i-pentane) or a mixed stream containing i-pentane and normal pentane (n-pentane). FIG. 3 is a process flow diagram depicting isoamylene production system 300 consistent with certain embodiments of the present disclosure. Pentanes feed stream 212 includes i-pentane. Pentanes feed stream 212 may include a mixture of i-pentane and n-pentane, in which a molar ratio of i-pentane to n-pentane ranges from 1:0.01 to 0.01:1, or from 1:0.1 to 0.1:1, or from 1:0.5 to 0.5:1, or from 1:0 to 0:1, for example. Pentanes feed stream 212 may be fed to bromination reactor 310. The i-pentane or mixture of i-pentane and n-pentane is reacted with bromine from bromine source stream 214 in bromination reactor 310 to form bromides. Bromine source stream 214 and pentanes feed stream 212 may be added separately to bromination reactor 310 or mixed prior to entry into bromination reactor 310.

Conditions for the bromination reaction in bromination reactor 310 are selected to: i) maximize the yield of t-pentyl bromide, 1-bromo-2-methylbutane or other monobromomethylbutanes, ii) minimize the formation of n-pentane bromides, and iii) minimize the formation of polybromides of i-pentene and n-pentane. Polybromides include dibromides, tribromides, and/or tetrabromides of i-pentene and n-pentane. Because the bromination reaction is exothermic, bromination reactor 310 may be cooled to maintain the bromination reaction within a desired temperature range. In certain embodiments, the bromination reaction is carried out in a shell and tube reactor in which bromine source stream 214 and pentanes feed stream 212 are introduced into Bromination reactor 310 at a temperature greater than or equal to 200° C., or equal to or greater than 60° C., or from 60° C. to 200° C. For example and without limitation, for isopentene, bromination may be carried out at a low temperature of (e.g., ~60° C.), which may reduce selectivity towards reaction with n-pentane. A bromination reaction may be carried out inside the tubes, and steam may then be generated on the shell side of the shell and tube reactor in order to limit the maximum temperature of bromination reactor 310 to the desired temperature range, such as 250° C. or lower, or 50° C. to 100° C. The generated steam may be used elsewhere in the process.

In certain embodiments of the present disclosure, a stoichiometric excess of the pentane may be used to decrease selectivity to polybromides and/or to limit temperature rise in the bromination reaction. In other embodiments of the present disclosure, the bromination reaction is carried out in one or more adiabatic reactors with cooling between the different adiabatic reactors. This cooling may be achieved using heat exchanger(s) or cold (~35° C.) bromine or pentanes. In certain other embodiments of this disclosure, cold (~35° C.) bromine is introduced at multiple positions along a length of bromination reactor 310 to keep the bromination reaction temperature within the desired range. In certain embodiments, this reaction is carried out at higher than atmospheric pressure. In certain other embodiments, this pressure is near that required for subsequent downstream separations. Having the pressure near that required for subsequent downstream separations may significantly improve the efficiency of the entire process by reducing or eliminating any required downstream compression prior to separation. Use of certain pressures may reduce the cooling used to condense the overhead stream in separation. In certain embodiments, cooling water may be used for condensing the overhead stream, rather than refrigeration. In other embodiments, refrigeration may be used for condensing the overhead stream. In certain embodiments, a combination of cooling water and refrigeration may be used for condensing the overhead stream. For example and without limitation, in some embodiments a pressure of at least 30 bar, or from 30 bar to 40 bar, or from 30 bar to 35 bar, or about 30 bar may be used for condensing the overhead stream. In embodiments in which the pressure is at least 30 bar, cooling water may be used for condensing the overhead stream. In embodiments in which the pressure is at least 30 bar, condensing the overhead stream in separation may be performed without use of refrigerant, such as propane. In some embodiments a pressure of from greater than 10 bar to less than 30 bar, or from 15 bar to 25 bar, or about 20 bar may be used for condensing the overhead stream. In embodiments in which the pressure is greater than 10 bar and less than 30 bar, a combination of cooling water and refrigerant, such as propane, may be used for condensing the overhead stream. In embodiments in which the pressure is greater than 10 bar and less than 30 bar, the overhead stream may be cooled to a temperature of from greater than 0° C. to less than 30° C., or from 15° C. to 25° C., or about 20° C. for condensing the overhead stream. In some embodiments a pressure of from greater than 0 bar to at most 10 bar; or from 5 bar to 10 bar, or from 7 bar to 10 bar may be used for condensing the overhead stream in separation. In embodiments in which the pressure is greater than 0 bar and at most 10 bar, a refrigerant, such as propane, may be used for condensing the overhead stream without use of cooling water. In embodiments in which the pressure is greater than 0 bar and at most 10 bar, the overhead stream may be cooled to a temperature of less than 0° C. In still other embodiments, bromination reactor 310 may be divided into a cooled section and an adiabatic section.

Bromides and HBr formed in bromination reactor 310 and unreacted pentanes are discharged from bromination reactor 310 as bromination effluent 216. Bromination effluent 216 enters separation section 312 where the reaction products of bromination reactor 310 are separated such as, for example, by distillation. For example and without limitation, bromination effluent 216 may be distilled or otherwise separated into two streams including: brominated compounds 218, which includes the bromides formed in the bromination reaction; and isomerization feed stream 220, which includes HBr, and unreacted n-pentane and i-pentane. In certain embodiments, isomerization feed stream 220 has a lower ratio of i-pentane to n-pentane than pentanes feed stream 212.

Isomerization feed stream 220 may be isomerized over an isomerization catalyst, such as, for example, $AlBr_3$ in isomerization reactor 314. Isomerization of isomerization feed stream 220 converts at least a portion of the n-pentane to i-pentane and increases the ratio of i-pentane to n-pentane over that in isomerization feed stream 220. The HBr in isomerization effluent 222 may be recovered in separation section 316 and transferred, for instance to HBr regeneration equipment 328 through HBr stream 224. The n-pentane and i-pentane in isomerization effluent 222 may be recycled to bromination reactor 310 through pentane recycle stream 226 from separation section 316*b*. In some embodiments, the amount of HBr present in isomerization feed stream 220 is reduced prior to being fed to isomerization reactor 314. For example and without limitation, isomerization feed stream 220 may be subjected separation, such as distillation, to remove at least a portion of HBr prior to entering isomerization reactor 314.

Following separation in separation section 312, brominated compounds 218 may be directed to separation section 318, where brominated compounds 218 are separated, such as by distillation, into two streams including: monobrominated stream 228, which may contain t-pentyl bromide and n-pentyl bromide; and recycle bromides stream 230, which may include isopentane polybromides.

Recycle bromides stream 230 may be partially hydrogenated with hydrogen from hydrogen stream 232 to t-pentyl bromide and n-bromopentane in hydrogenation reactor 320. Recycle bromides stream 230 may be completely hydrogenated with hydrogen from hydrogen stream 232 to i-pentane and n-pentane in the presence of a catalyst in hydrogenation reactor 320. For example and without limitation, hydrogenation catalyst may be Pd, Pt, Ni, Ru, Rh, Cu or another hydrogenation catalyst known to one skilled in the art. The hydrogenation reaction may be carried out in the presence of HBr to improve the selectivity to i-pentyl bromide and bromopentanes and minimize coke formation. Hydrogenation products stream 234 may be recycled to separation section 312. In certain embodiments (not shown) HBr may be recovered from hydrogenation products stream 234 and the remainder of hydrogenation products stream 234 may be recycled to separation section 312.

Monobrominated stream 228 may be fed to dehydrobromination reactor 322. In dehydrobromination reactor 322, t-pentyl bromide is converted to isoamylene. In certain embodiments of the present disclosure, this reaction is performed thermally in the absence of a catalyst, i.e., non-catalytically. However, in certain circumstances, a thermal reaction in dehydrobromination reactor 322 may be slow. Such slow reaction rates may require long residence times and/or high temperature in order to achieve suitable conversion. In some embodiments, the reaction in dehydrobromination reactor 322 may be carried out in the presence of a catalyst, such as a silica-based catalyst. One example of a suitable silica-based catalyst is WR Grace Silica 1151, available from W. R. Grace & Co. Another example of a suitable catalyst for dehydrobromination is Saint Gobain SG 61138. In order to shift the equilibrium in the desired direction, in certain embodiments, the reaction is carried out at a temperature of 250° C.-500° C. In certain embodiments, this reaction is carried out at higher than atmospheric pressure. In certain other embodiments, this pressure is near that required for subsequent downstream separations. Having the pressure near that required for subsequent downstream separations significantly improves the efficiency of the entire process by reducing or eliminating any required downstream compression prior to separation. Use of certain pressures may reduce the cooling used to condense the overhead stream in separation. In certain embodiments, cooling water may be used for condensing the overhead stream, rather than refrigeration. In other embodiments, refrigeration may be used for condensing the overhead stream. In certain embodiments, a combination of cooling water and refrigeration may be used for condensing the overhead stream. For example and without limitation, in some embodiments a pressure of at least 30 bar, or from 30 bar to 40 bar, or from 30 bar to 35 bar, or about 30 bar may be used for condensing the overhead stream. In embodiments in which the pressure is at least 30 bar, cooling water may be used for condensing the overhead stream. In embodiments in which the pressure is at least 30 bar, condensing the overhead stream in separation may be performed without use of refrigerant, such as propane. In some embodiments a pressure of from greater than 10 bar to less than 30 bar, or from 15 bar to 25 bar, or about 20 bar may be used for condensing the overhead stream. In embodiments in which the pressure is greater than 10 bar and less than 30 bar, a combination of cooling water and refrigerant, such as propane, may be used for condensing the overhead stream. In embodiments in which the pressure is greater than 10 bar and less than 30 bar, the overhead stream may be cooled to a temperature of from greater than 0° C. to less than 30° C., or from 15° C. to 25° C., or about 20° C. for condensing the overhead stream. In some embodiments a pressure of from greater than 0 bar to at most 10 bar, or from 5 bar to 10 bar, or from 7 bar to 10 bar may be used for condensing the overhead stream in separation. In embodiments in which the pressure is greater than 0 bar and at most 10 bar, a refrigerant, such as propane, may be used for condensing the overhead stream without use of cooling water. In embodiments in which the pressure is greater than 0 bar and at most 10 bar, the overhead stream may be cooled to a temperature of less than 0° C.

The effluent of dehydrobromination reactor 322, dehydrobromination effluent 235, includes isoamylene, HBr, and unconverted t-pentyl bromide. The dehydrobromination effluent 235 may be directed to separation section 324, where dehydrobromination effluent 235 is separated, such as by distillation, into crude product stream 236, which includes isoamylene and HBr; and dehydrobromination recycle 238, which includes t-pentyl bromide that was not converted in dehydrobromination reactor 322. In some embodiments, dehydrobromination effluent 235 may be rapidly cooled, for example, by contact with cold (~35° C.) t-pentyl bromide. Without being bound by theory, it is believed that rapid cooling reduces the formation of t-pentyl bromide through the reaction of HBr and isoamylene. Dehydrobromination recycle 238 may be recycled to dehydrobromination reactor 322.

Crude product stream 236 may be directed to separation section 326, where the isoamylene product is separated, such as by distillation, from HBr and recovered. HBr leaves separation section 326 as HBr stream 240. The isoamylene is discharged from separation section 326 through isoamylene product stream 242.

In certain embodiments of the present disclosure, HBr generated in isoamylene production system 300, such as HBr stream 240 and HBr stream 224, may be regenerated to form bromine, such as in HBr regeneration equipment 328. Regenerated bromine may be combined with bromine source stream 214.

The above examples demonstrate possible embodiments of the present disclosure. While the foregoing is directed to embodiments, versions and examples, which are included to enable a person of ordinary skill in the art to make and use the embodiments when the information in this patent is combined with available information and technology, the disclosure is not limited to only these particular embodiments, versions and examples. Other and further embodiments, versions and examples may be devised without departing from the basic scope thereof and the scope thereof is determined by the claims that follow.

What is claimed is:

1. A method comprising:
brominating a butanes feed stream comprising i-butane in a bromination reactor to form a bromination effluent stream comprising t-butyl bromide and unreacted i-butane;
dehydrobrominating the t-butyl bromide to form isobutylene and HBr, wherein the butanes feed stream and bromination effluent stream each further comprise n-butane
separating the butanes from the bromination effluent stream to form a brominated compound stream;
isomerizing at least a portion of the n-butane to form an isomerization effluent comprising i-butane and n-butane; and
feeding the i-butane and the n-butane of the isomerization effluent to the bromination reactor.

2. The method of claim 1, wherein the bromination effluent stream further comprises polybromides, wherein the method further comprises:
separating the polybromides from the brominated compound stream;
hydrogenating the polybromides to form a hydrogenation recycle stream; and
recycling the hydrogenation recycle stream to the bromination effluent stream.

3. The method of claim 2, wherein the hydrogenation recycle stream comprises t-butyl bromide and n-bromobutanes.

4. The method of claim 2, wherein the hydrogenation recycle stream comprises i-butane and n-butane.

5. The method of claim 1, wherein the isomerization effluent comprises HBr, and wherein the method further comprises separating the HBr from the isomerization effluent prior to feeding the i-butane and the n-butane of the isomerization effluent to the bromination reactor.

6. A method comprising:
brominating a butanes feed stream comprising i-butane in a bromination reactor to form a bromination effluent stream comprising t-butyl bromide and unreacted i-butane;
dehydrobrominating the t-butyl bromide to form isobutylene and HBr;
separating the butanes from the bromination effluent stream to form a brominated compound stream and an isomerization feed stream, wherein the isomerization feed stream comprises the butanes and HBr;
isomerizing at least a portion of the n-butane of the isomerization feed stream to form an isomerization effluent comprising i-butane and n-butane; and
feeding the i-butane and the n-butane of the isomerization effluent to the bromination reactor.

7. The method of claim 6, wherein the HBr is not separated from the isomerization feed stream prior to isomerizing at least a portion of the n-butane of the isomerization feed stream.

8. The method of claim 6, wherein at least a portion of the HBr is separated from the isomerization feed stream prior to isomerizing at least a portion of the n-butane of the isomerization feed stream.

9. A method comprising:
brominating a mixed pentanes feed stream comprising i-pentane and n-pentane in a bromination reactor to form a bromination effluent stream comprising t-pentyl bromide; and
dehydrobrominating the t-pentyl bromide to form isoamylene and HBr.

10. The method of claim 9, wherein the method further comprises:
separating the pentanes from the bromination effluent stream to form a brominated compound stream;
isomerizing at least a portion of the n-pentane to form an isomerization effluent comprising i-pentane and n-pentane; and
feeding the i-pentane and the n-pentane of the isomerization effluent to the bromination reactor.

11. The method of claim 10, wherein the bromination effluent stream further comprises polybromides, wherein the method further comprises:
separating the polybromides from the brominated compound stream;
hydrogenating the polybromides to form a hydrogenation recycle stream; and
recycling the hydrogenation recycle stream to the bromination effluent stream.

12. The method of claim 11, wherein the hydrogenation recycle stream comprises t-pentyl bromide and n-bromopentanes.

13. The method of claim 11, wherein the hydrogenation recycle stream comprises i-pentane and n-pentane.

14. The method of claim 9, wherein the isomerization effluent comprises HBr, and wherein the method further comprises separating the HBr from the isomerization effluent prior to feeding the i-pentane and the n-pentane of the isomerization effluent to the bromination reactor.

15. The method of claim 9, further comprising:
separating the pentanes from the bromination effluent stream to form a brominated compound stream and an isomerization feed stream, wherein the isomerization feed stream comprises the pentanes and HBr;
isomerizing at least a portion of the n-pentane of the isomerization feed stream to form an isomerization effluent comprising i-pentane and n-pentane; and
feeding the i-pentane and the n-pentane of the isomerization effluent to the bromination reactor.

16. The method of claim 15, wherein the HBr is not separated from the isomerization feed stream prior to isomerizing at least a portion of the n-pentane of the isomerization feed stream.

17. The method of claim 15, wherein at least a portion of the HBr is separated from the isomerization feed stream prior to isomerizing at least a portion of the n-pentane of the isomerization feed stream.

18. The method of claim 9, further comprising separating the isoamylene from the HBr.

19. The method of claim 9, wherein dehydrobrominating the t-pentyl bromide to form isoamylene and HBr is performed in the presence of a catalyst.

20. The method of claim 9, wherein dehydrobrominating the t-pentyl bromide to form isoamylene and HBr is performed in the absence of a catalyst.

21. The method of claim 9, wherein a molar ratio of i-pentane to n-pentane in the mixed pentanes feed stream ranges from 1:0.01 to 0.01:1.

* * * * *